United States Patent [19]

Picciola et al.

[11] Patent Number: 4,460,601

[45] Date of Patent: Jul. 17, 1984

[54] DIPEPTIDES HAVING A METHIONINE RESIDUE AND POSSESSING A PROTECTIVE ACTION FOR THE LIVER

[75] Inventors: Giampaolo Picciola; Franco Ravenna, both of Milan; Mario Riva, Monza, all of Italy

[73] Assignee: Maggioni Farmaceutici, S.p.A., Milan, Italy

[21] Appl. No.: 451,759

[22] Filed: Dec. 21, 1982

[30] Foreign Application Priority Data

Dec. 23, 1981 [IT] Italy ............................... 25804 A/81

[51] Int. Cl.³ ..................... A61K 31/27; A61K 31/38; C07C 153/00; C07C 103/52
[52] U.S. Cl. ............................... 424/300; 260/455 R; 260/546; 260/455 A; 260/112.5 R; 560/16; 560/148; 560/152; 560/153; 560/155; 560/157; 560/9; 562/556; 564/154; 564/162; 564/199; 549/71; 424/177; 424/275; 424/286; 424/309; 424/311; 424/320
[58] Field of Search ............... 260/455 R, 546, 455 A, 260/112.5 R; 562/556; 564/154, 162, 199; 560/16, 148, 152, 153, 155, 157, 9; 549/71; 424/177, 275, 286, 300, 309, 311; 428/320

[56] References Cited

U.S. PATENT DOCUMENTS

| 2,745,873 | 5/1956 | Callanan et al. | 562/556 |
| 4,091,024 | 5/1978 | Ondetti | 562/556 |
| 4,108,886 | 8/1978 | Ondetti | 260/455 R |
| 4,128,721 | 12/1978 | Ondetti | 260/455 R |
| 4,154,960 | 5/1979 | Ondetti et al. | 260/455 R |
| 4,176,235 | 11/1979 | Ondetti et al. | 260/455 R |

*Primary Examiner*—A. Siegel
*Attorney, Agent, or Firm*—Cushman, Darby & Cushman

[57] ABSTRACT

Dipeptides are claimed which consist of a mercaptoalkanoic acid and a derivative of said acid, namely an S-alkyl-, aralkyl-, aryl-, acyl- or aroyl derivative with methionine, a methionine ester or a methionine amide, as well as their salts with metallic cations and organic bases. These compounds have the property of protecting the liver against intoxications and have sedative and hypnotic properties.

14 Claims, No Drawings

DIPEPTIDES HAVING A METHIONINE RESIDUE AND POSSESSING A PROTECTIVE ACTION FOR THE LIVER

This invention relates to a series of dipeptides in which there is an amide bond between the carboxyl radical of a mercapto-alkanoic acid with a straight-line or branched chain composed of 1 to 6 carbon atoms, or an alkyl-, aralkyl-, aryl-, phenylacyl- or aroyl-derivative which contains sulphur, and the amine group of the D-, L- or DL-methionine, or an ester or amide thereof, as well as the salts of said dipeptides with metallic cations such as for example those of alkali metals or alkaline earth metals, or with pharmacologically acceptable organic bases such as choline, arginine and lysine.

The general formula of the compounds in question is:

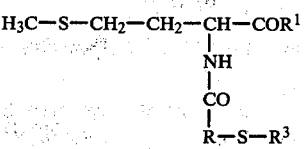

wherein R is a linear or a branched-chain alkyl having from 1 to 6 carbon atoms, $R^1$ is an $OR^2$ group or an $-N(R^2)_2$ group or an $-O-(CH_2)_n-N(R^2)_2$ group, wherein $R^2$ is a hydrogen or a linear or a branched-chain alkyl group having from 1 to 4 carbon atoms and n is variable from 1 to 3. $R_3$ has the same meaning as $R^2$ or can represent one group such as

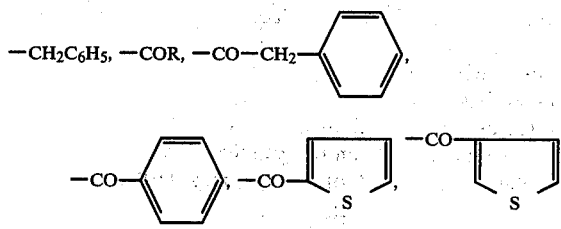

For the preparation of these compounds a few of the methods have been used, which are generally adopted for the formation of a peptide bond. As a rule, a compound of the formula

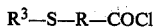

or

has been condensed with D-, L-, or DL-methionine, or with a methionine derivative of the formula:

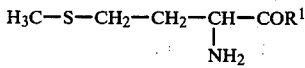

In the cases in which the acid chloride has been used, it has been possible to carry out the condensation directly, in the presence of a protonic acceptor, while, when starting from the carboxylic acid as such, it has been necessary to add a condensation agent such as dicyclohexylcarbodiimide, or it has been necessary to prepare a mixed anhydride beforehand with ethyl chlorocarbonate, and reacting the latter anhydride subsequently with the methionine derivative.

To obtain those compounds in which $R^3$ is H, the corresponding homologs in which $R^3$ is $-COC_6H_5$ have been saponified in the presence of an appropriate catalyst, such as an alkali metal alcoholate. If the molecule contains two chiral carbon atoms, the above mentioned derivatives may be present as mixtures of two erythro- and threo-racemates and these can be separated with conventional procedures. In their turn, the erythro- and the threo-forms can be split into their respective dextrorotatory and laevorotatory components by salification with an optically active acid.

The substances prepared according to the present invention have exhibited outstanding properties in protecting the liver function in animals which had been intoxicated by various toxic agents: more particularly in mice and rats which had been intoxicated with paracetamol or carbon tetrachloride, it has been observed that the increase of liver transaminases (SGOT and SGPT) is much lower than that which had been observed in non-treated animals.

The same compounds, in rats intoxicated with ethionine have very significantly reduced the increase of the liver triglycerides which is usually observed under such conditions.

Lastly, the compounds in question have exhibited both in mice and rats very pronounced hypnotic and sedative properties.

EXAMPLE 1

DL-N-[(3-benzoylmercapto)-propionyl]-methionine

An admixture of 32.58 g (0.22 mol) of DL-methionine, 150 mls of water, 214 mls (0.22 mol) of 1.02-normal NaOH and 250 mls of ethyl ether has been treated dropwise, between 0° C. and 3° C. and with vigorous stirring, with 25 g (0.1093 mol) of the 3-benzoyl-mercaptopropionic acid chloride in 100 mls of ether and, simultaneously, in order that the pH of the reaction environment may always be alkaline, with 9.2 g (0.11 mol) of $NaHCO_3$ in 100 mls of water. Once that the dropwise addition has been completed, stirring has been continued during 16 hours at room temperature. Upon separation of the organic phase, the aqueous fraction has been extracted with ethyl ether again and then made acidic with concentrated HCl (chilled) and extracted with ethyl acetate. The organic solution has been dried and evaporated to dryness under reduced pressures and the residue has been recrystallized from ethyl acetate.

Yield: 16 g (42.8% of theory), m.p. 84° C.–85° C.

EXAMPLE 2

DL-N-[(3-benzoylmercapto)-propionyl]-methionineamide

A solution of 7.35 g (0.035 mol) of 3-benzoylmercaptopropionic acid, 75 mls of anhydrous dimethylformamide and 3.54 g (0.035 mol) of triethylamine has been treated dropwise at −10° C. with stirring with 3.78 g (0.035 mol) of ethyl chlorocarbonate. Upon completion of dripping, stirring has been continued for 30 additional minutes at −10° C., whereafter the solution has been treated dropwise with 5.18 g (0.035 mol) of DL-methionineamide in 20 mls of anhydrous dimethylformamide (DMF) whereafter stirring has been continued for 16 hours at room temperature. The solution has subsequently been poured in 200 mls of water and extracted with ehtyl acetate, whereupon it has been washed with diluted HCl, water, diluted NaOH and water again, and dried over sodium sulphate and concentrated under reduced pressure. The residue has been recrystallized from isopropanol and has a m.p. of 139° C.–140.5° C., the yield being 3.2 g to 3.6 g (26.8% to 30.2% of theory).

EXAMPLE 3

DL-N-[(3-benzoylmercapto)-propionyl]methionine ethyl ester

To 16.8 g (0.08 mol) of 3-benzoylmercaptopropionic acid and 14.18 g (0.08 mol) of DL-methionine ethyl ester in 250 mls of chloroform, there have been added at 0° C. with stirring 16.50 g (0.08 mol) of dicyclohexylcarbodiimide and stirring has been continued during 24 hours at room temperature. The as-formed precipitate has been collected on a filter, washed with chloroform and the combined filtrates have been washed with water, diluted HCl, water, diluted NaOH, water, dried over sodium sulphate and evaporated to dryness under reduced pressures. The residue thus obtained has been recrystallized from isopropanol.

Yield: 24 g (81.1% of theory), m.p. 58' C.–61° C.

EXAMPLE 4

DL-N-(3-mercaptopropionyl)-methionineamide 3.4 g (0.01 mol) of DL-[N-(3-benzoylmercapto)-propionyl]methionineamide, dissolved in 80 mls of methanol have been treated dropwise at 20° C. in a hydrogen stream with 36 mls of 0.5-normal sodium methylate. Upon completion of the dripping, stirring has been continued for 2 additional hours, still in a hydrogen stream. Thereafter, the solution has been evaporated to dryness under reduced pressures and the residue taken up with water and extracted with ethyl ether. The aqueous phase has been filtered over charcoal, saturated with hydrogen sulphide, made acidic with concentrated HCl and extracted with ethyl acetate. After drying, the organic solution has been evaporated to dryness under reduced pressures and the residue has been recrystallized from benzene.

Yield: 1.4 g (59.3% of theory), m.p. 108° C.–110° C.

EXAMPLE 5

DL-N-[(3-benzylmercapto)-propionyl]methionine ethyl ester

A solution of 39.25 g (0.2 mol) of 3-benzylmercaptopropionic acid, 350 mls of dimethylformamide at 27.9 mls (0.2 mol) of triethylamine has been treated at −10° C. with stirring with 20 mls (0.2 mol) of ethyl chlorocarbonate. On completion of dripping, stirring has been continued for 30 minutes at −10° C. whereafter the solution has been treated dropwise with 35.44 g (0.2 mol) of the DL-methionine ethyl ester in 100 mls of dimethyl formamide and, on completion of this step, stirring has been continued for 16 additional hours at room temperature. The as-formed precipitate has been collected on a filter, washed with dimethylformamide and the combined filtrates have been evaporated to dryness under reduced pressures. The residue, dissolved in ethyl acetate, has been washed with diluted HC, water, diluted NaOH, water, dried over $Na_2SO_4$ and evaporated under reduced pressures. The oil thus obtained has been distilled and has a b.p. 215° C.–218° C. at 0.5 mmHg; yield 29 g (40.8% of theory).

EXAMPLE 6

DL-N-[(3-benzylmercapto)-propionyl]-methionine

To a solution of 12 g (0.034 mol) of DL-N-[(3-benzylmercapto)-propionyl]-methionine ethyl ester in 35 mls of ethanol, which is refluxed, there have been added during 3 hours 32.77 mls (0.0341 mol) of 1.03-normal NaOH. On completion of dripping, stirring and heating have been continued for one additional hour, whereafter the solution has been evaporated to dryness under reduced pressures, the residue taken up with water, extracted with ethyl acetate and combined water phases filtered on charcoal and made acidic with concentrated HCl. The as-formed precipitate has been collected on a filter, washed with water, dried in an oven at 50° C. and recrystallized from isopropanol.

Yield: 8.6 g (78% of theory), m.p. 95° C.–96° C.

EXAMPLE 7

DL-N-[(3-benzylmercapto)-propionyl]-methionineamide

A solution of 13 g (0.066 mol) of 3-benzylmercaptopropionic acid, 120 mls of anhydrous DMF and 9.20 mls (0.066 mol) of triethylamine have been treated dropwise at −10° C. with stirring with 6.3 mls (0.066 mol) of ethyl chlorocarbonate. On completion of dripping, stirring has been continued during 30 additional minutes at −10° C,, whereupon the solution has been treated dropwise with 9.81 g (0.066 mol) of DL-methionineamide in 35 mls of anhydrous DMF. On completion of dripping, stirring has been continued during 16 hours at room temperature, the solution has been filtered and the solvent distilled off under reduced pressures. The residue has been taken up with ethyl acetate, washed with diluted HCl, water, diluted NaOH, water and the organic phase has been dried over sodium sulphate and evaporated under reduced pressures, whereupon a precipitate is left which has been recrystallized from isopropanol.

Yield: 7 g (21.5% of theory), m.p. 110° C.–111.5° C.

EXAMPLE 8

DL-N-(2-mercaptopropionyl)-methionine (a) DL-N-[(2-benzoylmercapto)-propionyl]-methionine dicyclohexylamine salt An admixture of 15.63 g (0.1049 mol) of DL-methionine, 70 mls of water, 101.8 mls (0.1049 mol) of 1.02-normal NaOH and 150 mls of ethyl ether, has been treated dropwise between 0° C. and 3° C. with vigorous stirring, with 12 g (0.0524 mol) of the 2-benzoylmercaptopropionic acid chloride in 30 mls of ethyl ether and, simultaneously, in order to have a constantly alkaline pH in the reaction environment, with a solution of 4.4 g (0.0524 mol) of sodium bicarbonate in 100 mls of water. On completion of dripping, stirring has been continued for 16 hours at room temperature and, upon separation of the organic phase, the aqueous phase has been extracted again with ethyl ether, made acidic with chilled concentrated HCl, extracted with ethyl acetate and the organic phase has been dried and evaporated to dryness under reduced pressures. Dicyclohexylamine has been added to the oily residue which has previously been dissolved in ethyl ether until a complete precipitation of the salt has been obtained.

Yield: 13.2 g (24% of theory), m.p. 164° C.–167° C.

(b) DL-N-(2-mercaptopropionyl)-methionine 23 g (0.044 mol) of DL-N-[(2-benzoylmercapto)-propionyl]-methionine dicyclohexylamine salt, dissolved in 450 mls of methanol, have been treated dropwise at room temperature in a hydrogen stream with 193.6 mls (0.096 mol) of sodium methylate (0.5-normal soln.). On completion of dripping, stirring has been continued during 2 hours in a hydrogen stream and the solution has been evaporated to dryness under reduced pressures. The residue has then been taken up with water, extracted with ether and the water phase filtered on charcoal, saturated with hydrogen sulphide, made acidic with chilled concentrated HCl and extracted with ehtyl acetate. Upon drying, the organic solution evaporated to dryness under reduced pressures has given a solid residue which has been recrystallized from ethyl acetate.

Yield: 8.6 g (82.3% of theory), m.p. 108° C.–111° C.

EXAMPLE 9

DL-N-(2-mercaptopropionyl)-methionineamide (a) DL-N-[(2-benzoylmercapto)-propionyl]-methionineamide A solution of 33.6 g (0.16 mol) of 2-benzoylmercaptopropionic acid, 320 mls of DMF and 22.3 mls (0.16 mol) of triethylamine has been treated at −10° C. with stirring, with 16 mls (0.016 mol) of ethyl chlorocarbonate. On completion of dripping, stirring has been continued for 30 additional minutes at −10° C. whereafter the solution has been supplemented with 23.68 g (0.16 mol) of DL-methionineamide dissolved in 80 mls of DMF and stirring has been continued during 16 hours at room temperature. The precipitate has been collected on a filter, washed with DMF and the combined filtrates evaporated in dryness under reduced pressures and the residue has been dissolved in ethyl acetate. The organic solution washed with diluted HCl, water, diluted NaOH and dried over $Na_2SO_4$ and evaporated to dryness under reduced pressures, has given a solid which has been recrystallized from ethyl acetate.

Yield: 18.3 g (33.6% of theory), m.p. 156° C.–158° C.

(b) DL-N-(2-mercaptopropionyl)-methionineamide 17 g (0.05 mol) of DL-N-[(2-benzoylmercapto)-propionyl]-methionineamide and 400 mls of methanol have been treated dropwise at room temperature in a hydrogen stream with 120 mls of 0.5-normal sodium methylate. On completion of dripping, stirring has been continued during 2 hours in a hydrogen stream and the solution has been evaporated to dryness under reduced pressure. The residue has been taken up with water, extracted with ether and the aqueous phase filtered on charcoal, saturated with hydrogen sulphide, made acidic with chilled HCl and finally extracted with ethyl acetate. Upon drying the organic extract has been evaporated to dryness under reduced pressure and the residue recrystallized from ethyl acetate.

Yield: 7 g (59.3% of theory), m.p. 130° C.–131° C.

EXAMPLE 10

DL-N-[(2-benzoylmercapto)-propionyl]-methionine ethyl ester

A solution of 25.2 g (0.12 mol) of 2-benzoylmercaptopropionic acid, 21.27 g (0.12 mol) of the ethyl ester of DL-methionine and 360 mls of chloroform has been treated at 0° C. with 24.75 g (40.12 mols) of dicyclohexylcarbodiimide and, on completion of this step, the stirring was continued for 16 hours at room temperature. The as-formed precipitate has been collected on a filter, washed with chloroform and the combined solvents washed with water, diluted HCl, water, diluted NaOH and water. The organic phase, upon drying, has been evaporated to dryness under reduced pressures. An oily residue is obtained which has a b.p. of 220° C. at 0.5 mmHg.

Yield: 30 g (68% of theory).

EXAMPLE 11

DL-N-[(2-benzylmercapto)-propionyl]-methionine (a) DL-N-[(2-benzylmercapto)-propionyl]-methionine ethyl ester A solution of 77 g (0.392 mol) of 2-benzylmercaptopropionic acid, 700 mls of anhydrous DMF and 54.7 mls (0.392 mol) of triethylamine has been treated dropwise at −10° C. with stirring, with 39.2 mls of ethyl chlorocarbonate. On completion of dripping, stirring has been continued during 30 additional minutes at −10° C. whereafter the solution has been treated dropwise with 69.5 g (0.392 mol) of the DL-methionine ethyl ester in 200 mls of anhydrous DMF and, on completion of this step, stirring has been continued for 16 additional hours at room temperature, the solution has been filtered and evaporated under reduced pressures. The residue has then been dissolved in ethyl acetate and the solution washed with water, diluted HCl, water, diluted NaOH and water and, upon drying, evaporated to dryness under reduced pressures, giving an oily residue which has been distilled.

B.p. 220° C.–223° C. at 0.4 mmHg, Yield: 40 g (28.7% of theory).

(b) DL-N-[(2-benzylmercapto)-propionyl]-methionine

To a solution of 9.7 g (0.0273 mol) of DL-N-[(2-benzylmercapto)-propionyl]-methionine ethyl ester in 70 mls of methanol, refluxed, have been added, during 3 hours, 27.3 mls (0.0275 mol) of normal-NaOH. On completion of dripping, stirring and heating have been applied further for 1 hour, the solution has been evaporated to dryness under reduced pressures and residue taken up with water and extracted with ethyl acetate. The waters, filtered on charcoal and made acidic with 1:1 HCl, have been extracted with ethyl acetate which, upon drying over sodium sulphate, has been removed under reduced pressures to give a residue, recrystallized from isopropanol.

Yield: 5.2 g (58.2% of theory), m.p. 94° C.–96° C.

EXAMPLE 12

DL-N-[(2-benzylmercapto)-propionyl]-methionineamide

A solution of 19.6 g (0.1 mol) of 2-benzylmercaptopropionic acid, 180 mls of anhydrous DMF and 13.9 mls (0.1 mol) of triethylamine has been treated dropwise at −10° C. with stirring, with 9.51 mls (0.1 mol) of ethyl chlorocarbonate. On completion of dripping, stirring has been continued for 30 additional minutes at −10° C., whereafter the solution has been treated with a solution of 14.8 g (0.1 mol) of DL-methionineamide in 45 mls of anhydrous DMF, stirring being continued for 16 additional hours at room temperature. The solution has then been filtered and the solvent evaporated off under reduced pressures. The residue has been dissolved in ethyl acetate and the solution washed with diluted HCl, water, diluted NaOH, water and dried over sodium sulphate. The solid which has been obtained by evaporation under reduced pressures has been recrystallized from isopropanol.

Yield: 6.5 g (19.9% of theory).

EXAMPLE 13

DL-N-[(3-methylmercapto)-propionyl]-methionine ethyl ester 3.6 g (0.03 mol) of 3-methylmercaptopropionic acid and 5.31 g (0.03 mol) of DL-methionine ethyl ester dissolved in 100 mls of chloroform, have been treated with stirring at 0° C. with 6.18 g (0.03 mol) of dicyclohexylcarbodiimide and stirring has been continued for 16 additional hours at room temperature. The as-formed precipitate has then been collected on a filter, washed with chloroform, and the filtrate has been washed with water, diluted HCl, water, diluted NaOH, and water and dried (Na$_2$SO$_4$). By evaporating off chloroform under reduced pressures a residue has been obtained which has been recrystallized from isopropanol.

Yield: 4.6 g (54.8% of theory), m.p. 50° C.–51° C.

EXAMPLE 14

DL-N-[(2-acetylmercapto)-acetyl]-methionine ethyl ester 2 g (0.0149 mol) of 2-acetylmercaptoacetic acid and 2.64 g (0.0149 mol) of DL-methionine ethyl ester dissolved in 80 mls of chloroform have been treated at 0° C. with 3.07 g (0.0149 mol) of dicyclohexylcarbodiimide and stirring has been continued during 48 hours at room temperature. The as-formed precipitate has been collected on a filter, washed with chloroform and the combined organic filtrates have been washed with water, diluted HCl, water, diluted NaOH, water and dried and evaporated to dryness. The oily residue has been distilled.

B.p. 190° C. at 1 mmHg, Yield: 2 g (45.7% of theory).

EXAMPLE 15

DL-N-[(2-methylmercapto)-acetyl]-methionine ethyl ester 5.5 g (0.0519 mol) of 2-methylmercaptoacetic acid and 9.18 g (0.0519 mol) of DL-methionine ethyl ester, dissolved in 150 mls of chloroform, have been treated at 0° C. with 10.69 g (0.0519 mol) of dicyclohexylcarbodiimide and stirring has been continued during 48 hours at room temperature. The precipitate has been collected on a filter, washed with chloroform and the organic filtrates have been combined and washed with water, diluted HCl, water, diluted NaOH, water and, upon drying, they have been evaporated under reduced pressures to give an oily residue which distilled at 170° C./1 mmHg.

Yield: 10 g (72.6% of theory).

EXAMPLE 16

DL-N-[(2-benzoylmercapto)-acetyl]-methionine ethyl ester 2.3 g (0.0117 mol) of 2-benzoylmercaptoacetic acid and 2.07 g (0.0117 mol) of DL-methionine ethyl ester, dissolved in 50 mls of chloroform, have been treated at 0° C. with 2.4 g (0.0117 mol) of dicyclohexylcarbodiimide and stirring has been continued for 48 additional hours at room temperature. The precipitate has been collected to a filter, washed with chloroform and the organic filtrates have been combined and washed with water, diluted HCl, water, diluted NaOH and water and dried. By evaporation under reduced pressures a residue has been obtained, which has been recrystallized from isopropanol.

Yield: 3.2 g (77.1% of theory), m.p. 64° C.–65° C.

EXAMPLE 17

DL-N-[(3-acetylmercapto)-propionyl]-methionine ethyl ester 15 g (0.101 mol) of 2-acetylmercaptopropionic acid, 17.93 g (0.101 mol) of DL-methionine ethyl ester, dissolved in 200 mls of chloroform, have been treated at 0° C. with 20.88 g (0.101 mol) of dicyclohexylcarbodiimide and stirring has been continued for 16 additional hours at room temperature. The as-formed precipitate has been collected on a filter and washed with chloroform and the combined filtrates have been washed with water, diluted HCl, water, diluted NaOH and water and, upon drying, evaporated under reduced pressures. The residue has been distilled.

B.p. 205° C./1 mmHg, Yield: 20 g (64.5% of theory).

EXAMPLE 18

DL-N-[(2-thenoylmercapto)-propionyl]-methionine (a) 3-(2-thenoylmercapto)-propionic acid A mixture of 26.5 g (0.25 mol) of 3-mercaptopropionic acid, 150 mls of ethyl ether and 250 mls of 1-normal NaOH has been treated dropwise, the temperature being maintained between 0° C. and 5° C., with vigorous stirring, with 40.3 g of 2-thenoyl chloride (0.275 mol) in 80 mls of ethyl ether, while concurrently adding, so as to keep the pH of the reaction environment constantly alkaline, 31.5 g (0.36 mol) of NaHCO$_3$ in 800 mls of water. On completion of dripping, stirring has been continued for 16 additional hours at room temperature. Upon separation of the organic phase, the waters have been extracted with ethyl ether again, and then made acidic with 4-normal hydrochloric acid. The as-formed precipitate has been recrystallized from 70% ethanol.

Yield: 36 g (66% of theory), m.p. 116° C.–118° C.

(b) 3-(2-thenoylmercapto)-propionic acid chloride

To a slurry of 10 g (0.046 mol) of 3-(2-thenoylmercapto)-propionic acid in 20 mls of methylene chloride and 0.5 mls of dimethyl formamide there have been added slowly, while maintaining the temperature between 5° C. and 10° C., 5.77 g (0.048 mol) of thionyl chloride and the slurry has been refluxed. A homogeneous solution was the result and has been evaporated to dryness under reduced pressures. The residue has been taken up several times with methylene chloride and the latter solvent has been evaporated off under reduced pressures. The acid chloride thus obtained has been used as such for the next processing step.

(c) DL-N-[(2-thenoylmercapto)-propionyl]-methionine 13.8 g (0.0925 mol) of DL-methionine, 170 mls of ethyl ether and 92.5 mls of 1-normal NaOH have been treated dropwise, while maintaining the temperature between 0° C. and +5° C., with vigorous stirring, with the 3-(2-thenoylmercapto)-propionic acid chloride as obtained from the previous step (b), dissolved in 50 mls of ethyl ether and, concurrently, so as to keep the pH of the reaction medium constantly alkaline, with 3.9 g (0.0462 mol) of NaHCO₃ in 80 mls of water. On completion of dripping, stirring has been continued during 12 additional hours. Upon separation of the organic phase, the waters have been extracted with ethyl ether again, made acidic with 5-normal hydrochloric acid and extracted with ethyl acetate. The organic solution, upon drying over sodium sulphate, has been evaporated to dryness under reduced pressures.

We claim:

1. Novel chemical compounds having liver-protecting, desintoxicating, hypnotic and sedative properties having the general formula:

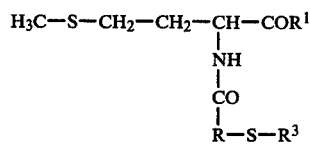

wherein R is a straight line or a branched alkyl radical having from 1 to 6 carbon atoms, $R^1$ is an $-OR^2$ group, or an $-N(R^2)_2$ group or an $-O-(CH_2)_n-N(R^2)_2$ group wherein $R^2$ is a hydrogen or a straight line or branched alkyl having from 1 to 4 carbon atoms and n may vary from 1 to 3, and $R^3$ is equal to $R^2$ or may represent a group such as

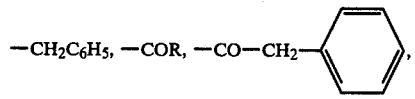

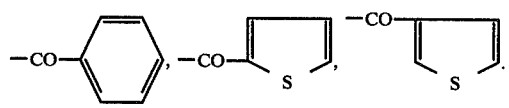

2. Salts of the compounds claimed in claim 1 with metallic cations selected from the group consisting of alkali metal and alkaline earth metals or with pharmacologically acceptable organic bases.

3. A compound according to claim 1 which is DL-N-[(3-benzoylmercapto)-propionyl]-methionine.

4. A compound according to claim 1 which is DL-N-[(3-benzoylmercapto)-propionyl]-methionineamide.

5. A compound according to claim 1 which is DL-N-[(3-benzoylmercapto)-propionyl]-methionine ethyl ester.

6. A compound according to claim 1 which is DL-N-(3-mercaptopropionyl)-methionine.

7. A compound according to claim 1 which is DL-N-(3-mercaptopropionyl)-methionineamide.

8. A compound according to claim 1 which is DL-N-(3-mercaptopropionyl)-methionine ethyl ester.

9. A compound according to claim 1 which is DL-N-[(3-methylmercapto)-propionyl]-methionine ethyl ester.

10. A compound according to claim 1 which is DL-N-[(2-methylmercapto)-acetyl]-methionine ethyl ester.

11. A compound according to claim 1 which is arginine salt of the DL-N-[(3-benzoylmercapto)-propionyl]-methionine.

12. A compound according to claim 1 which is choline salt of the DL-N-[(3-benzoylmercapto)-propionyl]-methionine.

13. A salt according to claim 2 which is a salt of choline, arginine, or lysine.

14. Pharmaceutical preparations for oral and parentheral administration, having liver-protecting, desintoxicating, hypnotic and sedative properties, containing any of the compounds claimed in claim 1 in unit dosage varying from 0.05 to 5 g.

* * * * *